United States Patent
Del Gatto et al.

(10) Patent No.: US 9,309,288 B2
(45) Date of Patent: *Apr. 12, 2016

(54) SELECTIVE $\alpha_v\beta_3$ RECEPTOR PEPTIDE ANTAGONIST FOR THERAPEUTIC AND DIAGNOSTIC APPLICATIONS

(71) Applicant: ADVANCED ACCELERATOR APPLICATIONS, Saint Genis Pouilly (FR)

(72) Inventors: Annarita Del Gatto, Torre del Greco (IT); Laura Zaccaro, Naples (IT); Carlo Pedone, Naples (IT); Michele Saviano, Milan (IT)

(73) Assignee: ADVANCED ACCELERATOR APPLICATIONS, Saint Genis Pouilly (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/016,020

(22) Filed: Aug. 30, 2013

(65) Prior Publication Data

US 2014/0094412 A1    Apr. 3, 2014

Related U.S. Application Data

(63) Continuation of application No. 12/089,709, filed as application No. PCT/EP2006/009733 on Oct. 9, 2006, now Pat. No. 8,546,526.

(60) Provisional application No. 60/725,294, filed on Oct. 12, 2005.

(51) Int. Cl.
| | |
|---|---|
| *A61K 38/00* | (2006.01) |
| *C07K 14/46* | (2006.01) |
| *C07K 7/64* | (2006.01) |
| *C07K 14/745* | (2006.01) |

(52) U.S. Cl.
CPC . *C07K 7/64* (2013.01); *C07K 14/46* (2013.01); *C07K 14/745* (2013.01); *A61K 38/00* (2013.01)

(58) Field of Classification Search
None
See application file for complete search history.

(56) References Cited

U.S. PATENT DOCUMENTS 8,546,526 B2 * 10/2013 del Gatto et al. ............. 530/317

OTHER PUBLICATIONS

Wierzbicka-Patynowski et al., J. of Bio. Chem., 1999, 274, 37809-814.*
Kumagai et al., Biochem. Biophys. Res. Commun., 1991, 177(1), 74-82.*
Marcinkiewicz et al., Blood, 90(4), 1997, 1565-75.*
Kumar, C.C. "Integrin $\alpha v\beta 3$ as a Therapeutic Target for Blocking Tumor-Induced Angiogenesis" *Current Drug Targets* (2003) 4:2, 123-131.
Gould, R.J. "Disintegrins: a family of integrin inhibitory proteins from viper venoms" *Proc Soc Exp Biol Med* (1990) 195:2, 168-171.
Dangles, O. et al. "Selective cleavage of the allyl and (allyloxy)carbonyl groups through palladium-catalyzed hydrostannolysis with tributyltin hydride. Application to the selective protection-deprotection of amino acid derivatives and in peptide synthesis" *J. Org. Chem.* 1987, 52:22, 4984-4993.

* cited by examiner

*Primary Examiner* — Karlheinz R Skowronek
*Assistant Examiner* — Roy Teller
(74) *Attorney, Agent, or Firm* — Steinfl & Bruno LLP

(57) ABSTRACT

The present invention is related to new peptide antagonists of $\alpha_v\beta_3$ receptor, designed on the basis of the crystal structure of integrin $\alpha_v\beta_3$ in complex with c(RGDf[NMe]V) and the NMR structure of echistatin. These peptides are potent and selective antagonists of the $\alpha_v\beta_3$ receptor and can be used as novel anticancer drugs and/or new class of diagnostic non-invasive tracers as suitable tools for $\alpha_v\beta_3$-targeted therapy and imaging.

11 Claims, 3 Drawing Sheets echiL      [1]KRGDeMDDPGRNPHKGPAT[19]

echi6-19      M[6]DDPGRNPHKGPAT[19]

echi11-19      [11]RNPHKGPAT[19]

SELECTIVE α$_v$β$_3$ RECEPTOR PEPTIDE ANTAGONIST FOR THERAPEUTIC AND DIAGNOSTIC APPLICATIONS

CROSS REFERENCE TO RELATED APPLICATIONS

This application is a U.S. Continuation application of Ser. No. 12/089,709 filed on Apr. 9, 2008, which is the national phase of International Application PCT/EP2006/009733 filed on Oct. 9, 2006, which, in turn, claims priority to U.S. Provisional Application 60/725,294 filed on Oct. 12, 2005, each of which are herein incorporated by reference in its entirety.

BACKGROUND OF THE INVENTION

Integrins are members of a family of heterodimeric transmembrane cell surface receptors that play a crucial role in cell-cell and cell-matrix adhesion processes (Hynes, R. O. *Cell* 1992, 69, 11-25). These receptors consist of an α- and a β-subunit, which non-covalently associate in defined combinations (Eble, J. A. *Integrin-Ligand Interaction;* Springer: Heidelberg, 1997; pp 1-40). Most of them recognize the Arg-Gly-Asp (RGD) triad found in many extracellular matrix proteins (i.e vitronectin) (Serini, G.; et al. A sticky business. *Exp. Cell. Res.* 2005, in press) and snake venom disintegrins (Ruoslahti, E.; Pierschbacher, M. *Cell* 1986, 44, 517-518; D'Souza, S. E.; et al. *Trends Biochem. Sci.* 1991, 16, 246-250; Gould, R. J.; et al. *Proc. Soc. Exp. Biol. Med.* 1990, 195, 168-171). Even if different integrins recognize different proteins containing the RGD sequence, several studies have demonstrated that the amino acid residues flanking the RGD sequence of high-affinity ligands modulate their specificity of interaction with integrin complexes. Despite numerous studies reported in the literature, ligand selectivity toward different integrin subtypes is still a challenging problem mainly because most of the 3D-structures of integrin subtypes remain unknown (Marinelli, L.; et al. *J. Med. Chem.* 2004, 47, 4166-4177).

An extensively studied member of this receptor class is integrin α$_v$β$_3$. This integrin is strongly expressed on activated endothelial and melanoma cells, in contrast, it is weakly expressed in quiescent blood vessels and pre-neoplastic melanomas (Hood, J. D.; Cheresh, D. A. *Nat. Rev. Cancer* 2002, 2, 91-100). Along with α$_v$β$_5$ integrin, α$_v$β$_3$ is reported to be involved in physiological processes including angiogenesis and tissue repair as well as pathological conditions such as tumor induced angiogenesis (Eliceiri, B. P.; Cheresh, D. A. *J. Clin. Invest.* 1999, 103, 1227-1230; Kumar, C. C. *Curr. Drug Targets* 2003, 4, 123-131), tumor cell migration and invasion (Clezardin, P. *Cell. Mol. Life. Sci.* 1998, 54, 541-548). Despite the fact that both integrins promote cell attachment to vitronectin and participate in the same processes, they are reported to be structurally designed to respond to different signaling events. Previous studies provided evidence that bFGF-induced angiogenesis is mediated by α$_v$β$_3$ whereas VEGF-induced angiogenesis is mediated by α$_v$β$_5$ (Friedlander, M.; et al. *Science* 1995, 270, 1500-1502). Melanoma cells expressing α$_v$β$_3$ migrate in vitro and metastasize in vivo without the need for exogenous cytokine stimulation (Filardo, E. J.; et al. *J Cell Biol.* 1995, 130, 441-450). Conversely, tumor cells expressing α$_v$β$_5$ integrin require a tyrosine kinase receptor-mediated signaling event for motility on vitronectin and in vivo dissemination (Brooks, P. C.; et al *J Clin Invest.* 1997, 99, 1390-1398). While α$_v$β$_5$ is widely expressed by many malignant tumor cells, α$_v$β$_3$ has a relatively limited cellular distribution compared with that of α$_v$β$_5$ (Pasqualini, R.; et al. *J. Cell Science* 1993, 105, 101-111; Walton, H. L.; et al. *J. Cell. Biochem.* 2000, 78, 674-680.). Therefore, in order to target α$_v$β$_3$-mediated processes for diagnostic or therapeutic purposes, the development of new compounds that can discriminate between α$_v$β$_3$ and α$_v$β$_5$ is required.

To date, various therapeutic candidates, including antibodies (Gutheil, J. C. et al. *Clin. Cancer Res.* 2000, 6, 3056-3061), small molecules (Miller, W. H.; et al. *Drug Discov. Today* 2000, 5, 397-408; Marugan, J. J.; et al. *J. Med. Chem.* 2005, 48, 926-934), peptidomimetics (Sulyok, G. A.; et al. *J. Med. Chem.* 2001, 44, 1938-1950; Belvisi, L.; et al. *Org. Lett.* 2001, 3, 1001-1004), and cyclic peptides (Mitjans, F. et al. *Int. J. Cancer* 2000, 87, 716-723; Dechantsreiter, M. A.; et al *J. Med. Chem.* 1999, 42, 3033-3040) have been clinically evaluated and shown to successfully modulate α$_v$β$_3$-mediated processes. So far, the pentapeptide cyclo (-Arg-Gly-Asp-D-Phe-NMeVal-), referred to as c(RGDf[NMe]V) (Eskens, F. A.; et al *Eur. J. Cancer* 2003, 39, 917-926), is one of the most active α$_v$β$_3$ antagonists reported in the literature. Previous studies have demonstrated a higher affinity of this peptide for integrin α$_v$β$_3$ as compared to α$_v$β$_5$ and have reported inhibition of α$_v$β$_3$-mediated cell adhesion with IC$_{50}$ values in the micromolar range when assayed in different tumor cell lines (Goodman, S. L.; et al. *J. Med. Chem.* 2002, 45, 1045-1051).

The crystal structures of the extracellular segment of integrin α$_v$β$_3$ in its unligated state and in complex with c(RGDf[NMe]V) and the docking studies on α$_v$β$_3$ integrin ligands have shown that the main interactions are between the positively charged arginine and the α-subunit and between the anionic aspartic acid and the β-subunit (Marinelli, L.; et al. *J. Med. Chem.* 2003, 46, 4393-404; Xiong, J. P. et al. Crystal structure of the extracellular segment of integrin α$_v$β$_3$. *Science* 2001, 294, 339-345; Xiong, J. P.; et al. *Science* 2002, 296, 151-155), and that selectivity between different subunits is achieved by the RGD sequence conformation. Previous studies also reported that echistatin, the smallest (49 residues) of the viper (*Echis carinatus*) disintegrins, is a potent antagonist of the integrins α$_v$β$_3$, α$_5$β$_1$ and α$_{IIb}$β$_3$ (Wierzbicka-Patynowski, I.; et al. *J. Biol. Chem.* 1999, 274, 37809-37814) and that the amino acids adjacent to the RGD motif together with the 41-49 C-terminal residues appear to be critical for the selective recognition of integrins. Mutation and photoaffinity cross-linking experiments, and NMR conformational analysis combined with docking studies Yahalom, D.; et al. *Biochemistry* 2002, 41, 8321-8331; Saudek, V.; et al. *Biochemistry* 1991, 30, 7369-7372), have provided evidence that the C-terminal region of echistatin binds to a site within the β$_3$ subunit of the α$_v$β$_3$ receptor, which is distinct from the sites that bind residues flanking the RGD triad in small peptide ligands.

SUMMARY OF THE INVENTION

This invention concerns peptide or peptidomimetic compounds, containing the Arg-Gly-Asp sequence, as potent and selective antagonists of the α$_v$β$_3$ receptor: the compounds of the invention may be used as novel anticancer drugs and/or new class of diagnostic noninvasive tracers as suitable tools for α$_v$β$_3$-targeted therapy and imaging.

DETAILED DESCRIPTION OF THE INVENTION

Figure 1:
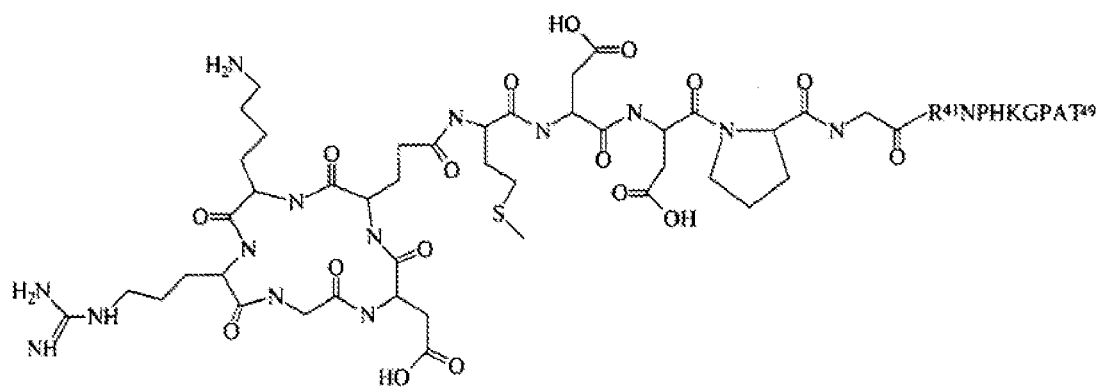
FIG. 1. Is a schematic representation of the synthesized peptides. including RGDechi, echiL (SEQ ID NO: 1), echi6-19 (SEQ ID NO: 2) and echi11-19 (SEQ ID NO: 3).

The compounds of the invention have the following formula (I):

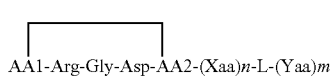

AA1-Arg-Gly-Asp-AA2-(Xaa)$n$-L-(Yaa)$m$    (I)

wherein:

AA1 is an alpha amino acid containing at least three functional groups, selected in the group of Cys, Asp, Glu, Lys, Orn, Pen, Dab or Dap;

AA2 is an alpha amino acid containing at least three functional groups, selected in the group of Cys, Asp, Glu, Lys. Orn, Pen, Dab or Dap;

L is a linker sequence consisting of a number of amino acid residues comprised between 0 and 2, such as the sequence PG;

(Xaa)n is an amino acid sequence in which n ranges from 1 to 3, which sequence is substantially homologue to that of sequence 28-30 of Echistatin: MDD.

(Yaa)m is an amino acid sequence in which m ranges from 2 to 9, which sequence is substantially homologue to that of C-terminus (41-49) of Echistatin: RNPHKGPAT (SEQ ID NO: 3).

The cyclic structure of the pentapeptide is obtained via the formation of a peptide bond between the CO of AA1 and the NH of AA2.

AA2 is preferably a D-aminoacid.

Preferred (Xaa)n sequence is MDD whereas preferred (Yaa)m sequence is RNPHKGPAT (SEQ ID NO: 3).

The Xaa group is linked to AA2 via formation of an amide bond between the side chain of AA2 and the N-terminal of Xaa.

The peptides of the invention have either free or acetylated amino groups at the N-terminus and either free or amidated carboxyl groups at the C-terminal position; one or two more amino acid residues can be added onto the C-terminal end.

The invention also relates to compounds of formula (I) which are labelled, either with the use of a chelating group or directly, with radioactive or paramagnetic metals or radioactive halogens and the salts thereof with physiologically acceptable organic or inorganic bases or with anions of physiologically acceptable organic or inorganic acids.

For the compounds of the invention which contain amino acids, the amino acid residues are denoted by single-letter or three-letter designations following conventional practices. All of the amino acids used in the present invention may be either the D- or L-isomer. The L-isomers are preferred when not otherwise specified. Commonly encountered amino acids which are not gene-encoded may also be used in the present invention.

The term "substantially homologous" means that the amino acid sequence of a particular compound shows a substantial correspondence to the amino acid sequence of C-terminal sequence of echistatin, in which at least three aminoacids in the sequences can be mutated with any aminoacids, preferably by conservative substitutions. The term "any amino acid" used above refers to the L and D isomers of the natural amino acids and "non-protein" amino acids commonly used in peptide chemistry to prepare synthetic analogs of natural peptides, such as alpha amino acids substituted and not substituted at the alpha and beta positions of the L and D configurations, and unsaturated alpha and beta amino acids. Examples of "non-proten" amino acids are norleucine, norvaline, alloisoleucine, allothreonine, homoarginine, thioproline, dehydroproline, hydroxyproline, pipecolic acid, azetidine acid, homoserine, cyclohexylglycine, alpha-amino-n-butyric acid, cyclohexylalanine, aminophenylbutyric acid, phenylalanine mono and di-substituted at the positions ortho, meta and para of the aromatic ring, O-alkylated derivatives of serine, threonine and tyrosine, Salkylated cysteine, epsilon-alkylated lysine, delta-alkylated ornithine, aromatic amino acids, substituted at the positions meta or para of the ring such as phenylalanine-nitrate, -sulfate, -phosphate, -acetate, -carbonate, -methylsulfonate, -methylphosphonate, tyrosine-sulfate, -phosphate, -sulfonate, -phosphonate, para-amido-phenylalanine, C-alpha,alpha-dialkylated, amino acids such as alpha,alpha-dimethylglycine (Aib), alpha-aminocyclopropanecarboxylic acid (Ac3c), alpha-amino cyclobutane-carboxylic acid (Ac4c), alphaminocyclopentanecarboxylic acid (Ac5c), alpha-aminocyclohexanecarboxylic acid (Ac6c), diethylglycine (Deg), dipropylglycine (Dpg), diphenylglycine (Dph). Examples of beta-amino acids are beta-alanine (beta-Ala), cis and trans 2,3-diaminopropionic acid (Dap). Other non-protein amino acids are identified on the website http://CHEMLIBRARY.BRI.NRC.CA/.

The peptide or peptidomimetic compounds of the present invention can be synthesized by conventional methods used in ordinary peptide chemistry, as described, for example, in M. Bodansky and M. A. Ondetti, Peptide Synthesis, published by Interscience Publishing Co., New York, 1966; F. M. Finn and K. Hofmann, The Proteins, volume 2, edited by H. Neurath, R. L. Hill, Academic Press Inc., New York, 1976; Nobuo Izumiya et al., Peptide Synthesis, published by Maruzen Co., 1976; Nobuo Izumiya et al., Fundamental Peptide Synthesis and Experiment, published by Maruzen Co., 1985; Lecture Series on Biochemical Experiment, edited by the Association of Biochemistry, Japan, volume 1, "Chemistry of Protein IV", chapter II, Haruaki Yajima, Peptide Synthesis, 1977.

The peptide can be synthesized by selecting the liquid phase method or the solid phase method, depending on the structure of the peptide. The peptide compounds can also be synthesized by combining the solution and the solid phase methods.

The compounds of the invention are purified by reverse-phase high pressure liquid chromatography. The compounds are identified by mass spectrometry, amino acid analysis, NMR spectroscopy.

The invention also refers to compounds of general formula (II):

wherein A is a peptide of general formula (I); z is an integer between 0 and 5; Y is a spacer chain respectively bonded to one of the functionalities present on the side chains of the individual amino acids present in peptide A, or to an N-terminal (—NH$_2$) group or a C-terminal (—CO$_2$H) group of A, and to C; when z is an integer between 2 and 5, units Y may be the same or different from each other;

Y is preferably a group of formula (III):

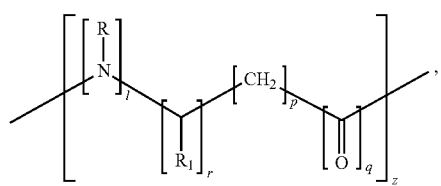

wherein:

r, l, and q are each independently 0 or 1, and p are an independently an integer from 0 to 10, provided that at least one of l, r and q is other than zero;

R is hydrogen;

R1 is a hydrogen or a —CH$_3$ group;

C may be a chelating agent, covalently bound to the spacer Y or directly to peptide A, or to more than one amino acid units of peptide A, which is able to complex a paramagnetic metal or a radioisotopes.

Preferred chelating groups are selected from the group consisting of:

a residue of a polyaminopolycarboxylic acid and the derivatives thereof, in particular selected from diethylenetriaminopentaacetic acid (DTPA), 1,4,7,10-tetraazacyclododecane-1,4,7,10-tetraacetic acid (DOTA), 1,4,7,10-tetraazacyclododecane-1,4,7-triacetic acid (D03A), [10-(2-hydroxypropyl)-1,4,7,10-tetraazacyclododecane-1,4,7-triacetic acid (HPDO3A), 4-carboxy-5,8,11-tris(carboxymethyl)-1-phenyl-2-oxa-5,8,11-triazamidecan-13-oic acid (BOPTA), N-[2-[bis(carboxymethyl)amino]-3-(4-ethoxyphenyl)propyl]-N-[2-[bis(carboxymethyl) amino] ethylglycine (EOB-DTPA), N,Nbis[2[(carboxymethyl)[(methylcarbamoyl)methyl]amino]ethyl]-glycine (DTPA-BMA), 2-methyl-1,4,7,10-tetraazacyclododecane-1,4,7,10-tetraaceti acid (MCTA), (α,α',α",α'")-tetramethyl-1,4,7,10-tetraazacyclododecane-1,4,7,10-tetracetic acid (DOTMA); or is the residue of a polyaminophosphate acid ligand or derivatives thereof, in particular N,N'-bis-(pyridoxal-5-phosphate)ethylenediamine-N,N'-diacetic acid (DPDP) and ethylenedinitrilotetrakis(methylphosphonic) acid (EDTP); or is the residue of a polyaminophosphonic acid ligand and derivatives thereof, or polyaminophosphinic acid and derivatives thereof, in particular 1,4,7,10-tetraazacyclodo decane-1,4,7,10-tetrakis[methylene (methylphosphonic)]acid and 1,4,7,10-tetraazacyclododecane-1,4,7,10-tetrakis[methylene-(methylphosphinic) acid; or is the residue of macrocyclic chelants such as texaphrines, porphyrins, phthalocyanines; or is N,N-bis[2-[bis(carboxymethyl)amino]ethyl]L-glutamic acid (DTPA-GLU) or DTPA conjugated with Lys (DTPA-Lys). Other chelating groups are reported in the publication "Radionuclide Peptide Cancer Therapy" edited by M. Chinol and G. Paganelli, Taylor & Francis CRC Press, 2006 (ISBN: 0824728874).

C may also be a radiotracer for nuclear medicine, such as F18-galacto group, covalently bound to spacer Y or directly to peptide A, or to more than one amino acid unit of peptide A. Other radiotracers are those reported in the publication "Radionuclide Peptide Cancer Therapy" edited by M. Chinol and G. Paganelli, Taylor & Francis CRC Press, 2006 (ISBN: 0824728874).

These peptides can be used in MRI and in Nuclear Medicine application for the diagnosis and treatment of cancers.

The invention accordingly provides also method of treatment of a disorder comprising the administration to an individual suffering from such disorder of a therapeutically effective amount of the $\alpha_v\beta_3$ antagonist of formula I or II.

Examples of specific disorders include pathologies are related to angiogenesis and metastasis, such as breast cancer, musculoskeletal tumors, melanoma, head and neck cancer, human glioma, cervical cancer, vascular restenosis, osteoporosis, rheumatoid arthritis.

More particularly, the compounds of the invention are able to decrease the proliferation of tumor cells and/or to modulate pathologic angiogenesis.

The compounds of the invention may also be used in the diagnosis of disorders using MRI and Nuclear Medicine methods (PET, SPECT etc) by administering an effective amount thereof to a subject, particularly for the diagnosis of diseases related to angiogenesis and metastasis such as breast cancer, musculoskeletal tumors, melanoma, head and neck cancer, human glioma, cervical cancer, vascular restenosis, osteoporosis, rheumatoid arthritis.

The invention also concerns a diagnostic kit comprising the $\alpha_v\beta_3$ antagonist as defined above for the early detection in plasma of pathologies, such as breast cancer, musculoskeletal tumors, melanoma, head and neck cancer, human glioma, cervical cancer, vascular restenosis, osteoporosis, rheumatoid arthritis.

The invention is illustrated in more detail by the following example.

EXAMPLE

The peptide having the sequence reported in FIG. 1, and hereinafter referred to as RGDechi, is a bifunctional chimeric molecule containing a cyclic RGD motif and a sequence corresponding to echistatin C-terminal tail connected by a linker. In order to evaluate the activity of the bifunctional molecule RGDechi, echiL (SEQ ID NO: 1), echi11-19 (SEQ ID NO: 3) and echi6-19 (SEQ ID NO: 2) (FIG. 1) were designed. Echi11-19 (SEQ ID NO: 3) and echi 6-19 (SEQ ID NO: 2) encompass the 11-19 and 8-19 RGDechi sequences respectively, and echiL (SEQ ID NO: 1) corresponds to the linear precursor of RGDechi.

Synthesis: All peptides were synthesized on a ABI433A automated peptide synthesizer using Fmoc solid-phase strategy (0.25 mmol). The synthesis was carried out with Novasyn TGA resin (substitution 0.29 mmol g$^{-1}$), using all standard amino acids except for Fmoc-D-Glu-OAll in order to insert the D-Glu$^5$ residue in the peptide sequence by its carboxyl side chain. The first amino acid was bound onto the resin by treatment with Fmoc-Thr(tBu)-OH (5 eq)/MSNT (5 eq)/MeIm (3.75 eq) in DCM for 3 h. The Fmoc deprotection step was performed with 30% piperidine in DMF for 10 min and active ester coupling reactions were carried out under a four-fold excess of amino acid and HBTU (4 eq)/HOBt (4 eq)/DIPEA (8 eq) in DMF (Fields, C. G.; et al *Pept. Res.* 1991, 4, 95-101). Each coupling was repeated twice for 1 h followed by a capping step (5 min) performed with acetic anhydride/DIPEA/DMF (2.6:4.8:92.6 v/v/v).

After the Arg[11] coupling reaction an aliquote of the peptidyl-resin was removed to yield the echi11-19 peptide. At the end of the Met[6] coupling, another part of the resin was removed to obtain echi6-19 peptide. During the RGDechi synthesis before the Fmoc deprotection of Lys[1], selective α-carboxyl deprotection of D-Glu[5] residue from allyl group was carried out by treatment of the peptidyl-resin with $PhSiH_3$ (24 eq)/$Pd(PPh_3)_4$ (0.25 eq) in DCM. Before the final cyclization the resin was divided in two parts, in order to obtain echiL and to continue the synthesis of RGDechi. The cyclization between αNH of Lys[1] and αCO of D-Glu[5] was performed with PyBop (1.5 eq)/HOBt (1.5 eq)/DIPEA (2 eq) in DMF.

The peptides were cleaved off the resin and deprotected using a mixture of TFA/$H_2O$/EDT/TIS (94:2.5:2.5:1 v/v/v/v). The resins were then filtered and the peptides were precipitated using cold anhydrous diethyl ether.

The crude products were purified by preparative RP-HPLC on the Shimadzu LC-8A system, equipped with an Uv-V is detector SPD-10 A using a Phenomenex C18 column (21× 250 mm; 15 µm; 300 A) and a linear gradient of $H_2O$ (0.1% TFA)/$CH_3CN$ (0.1% TFA) from 5% to 70% of $CH_3CN$ (0.1% TFA) in 30 min at flow rate of 20 mL/min. The purified peptides were characterized using MALDI-TOF spectrometry on a MALDI-TOF Voyager-DE (Perseptive Biosystem) spectrometer, which gave the expected molecular ion peaks [M-H]+ of 2061.2, 978.1, 1493.6, 2079.2 for RGDechi, echi11-19 (SEQ ID NO: 3), echi 6-19 (SEQ ID NO: 2) and echiL (SEQ ID NO: 1), respectively.

All peptides were synthesized by the solid-phase method using Fmoc chemistry. All aminoacids were coupled according to the HBTU/HOBt/DIPEA procedure (Fields, C. G.; et al *Pept. Res.* 1991, 4, 95-101). Final deprotection and cleavage form the resin were achieved with TFA and scavengers. During the RGDechi synthesis, before the Fmoc deprotection of Lys[1], α-carboxyl selective deprotection of the D-Glu[5] residue from the allyl group was carried out by treatment of the peptidyl-resin with $PhSiH_3$/$Pd(PPh_3)_4$/DCM (Dangles, O. et al. *J. Org. Chem.* 1987, 52, 4984-93). Before the final cyclization, the resin was split in two parts, to obtain echiL and to continue the synthesis of RGDechi. The cyclization between the αNH group of Lys[1] and the αCO group of D-Glu[5] was performed with PyBop/HOBt/DIPEA (Coste, J. et al. *Tetrahedron Lett.* 1990, 31, 205-8) in DMF.

The purity and the identity of the peptides were confirmed by analytical RP-HPLC and MALDI-TOF mass spectrometry. The overall yields of RGDechi, echiL (SEQ ID NO: 1), echi6-19 (SEQ ID NO: 2) and echi11-19 (SEQ ID NO: 3), purified by preparative RP-HPLC, were 24%, 30%, 54% and 58%, respectively.

Cell Adhesion and Competitive Assay: Human erythroleukemia K562 cells, stably cotransfected with cDNA of $α_v$ or $α_{IIb}$ subunit and $β_3$ or $β_5$ subunits, were kindly provided by Dr. S. D. Blystone (SUNY Upstate Medical University, Syracuse, N.Y.). Cells were maintained in Iscove's Modified Dubecco's Medium (IMDM) supplemented with 10% heat-inactivated fetal bovine serum, 100 IU/ml penicillin, 50 µg/mL streptomycin and 500 µg/mL G418 in a humidified incubator with 5% $CO_2$ at 37° C. Expression of $α_vβ_3$, $α_vβ_5$ and $α_{IIb}β_3$ in the transfected clones was confirmed by flow cytometry using FITC-labeled LM609, P1F6 and A2A9/6 monoclonal antibodies. Cells were used to determine affinity for $α_vβ_3$ and cross-reactivity with $α_vβ_5$ and $α_{IIb}β_3$ integrin. RGDechi was tested for its ability to inhibit cell adhesion to immobilized vitronectin or fibrinogen and to compete for the binding with $^{125}$I-labeled cyclic RGD peptide. Other cyclic peptides, such as c(RGDfV) and its variant c(RGDyV) as well as specific sequence of RGDechi, were used for comparison.

Cell adhesion assays were performed as previously described (Chiaradonna, F.; et al *EMBO J.* 1999, 18, 3013-3023). Briefly, 24-well flat-bottom plates were incubated overnight with 5 µg/mL vitronectin. The pre-coated plates were rinsed with PBS, incubated for 1 h at 23° C. with 1% heat-denatured bovine serum albumin, and rinsed again. Then, $α_vβ_3$ overexpressing K562 cells were incubated with various concentrations of cyclic RGD peptides or diluents for 1 h at 4° C. Peptide-treated cells (0.2-0.5×106/100 µL/well) were seeded onto pre-coated plates and allowed to adhere for 1 h at 37° C. in 5% $CO_2$. Non-adherent cells were removed with gentle washing, whereas adherent cells were detached by trypsinization and counted. Three different adhesion assays were performed in duplicates. The results of each assay were analysed by GraphPad Prism Software Inc, San Diego, Calif., using the nonlinear regression least-squares method, to estimate the $IC_{50}$ values for each peptide.

To test the selectivity of the novel peptide, $α_vβ_5$ or $α_{IIb}β_3$ overexpressing K562 cells were incubated with increasing concentration of c(RGDfV) or RGDechi and cell adhesion was determined as previously described using vitronectin or fibrinogen as indicated.

The peptide c(RGDyV) was labeled with $^{125}$I using the Iodo-Gen method as previously described (Del Vecchio, S. et al. *Cancer Res.* 1993, 53, 3198-3206). Briefly, 100 µg of peptide were reacted with 500 µCi of Na $^{125}$I and 12 µg of Iodo-Gen. After 15 min the reaction was stopped by the addition of 1 µmol of N-acetyltyrosine. The radiolabeled peptide was purified by unbound iodide by size-exclusion polyacrylamide chromatography (Felding-Habermann, B. *Pathophysiol. Haemost. Thromb.* 2003, 33 Suppl 1, 56-58). The radiolabeled product contained less than 3% of free iodide as assessed by HPLC. Cells (1×10[6]) were then incubated with $^{125}$I-labeled c(RGDyV) in the presence or absence of a large excess of unlabeled competitors for 1 h at 4° C. After extensive washing, cell-associated radioactivity was determined by γ-counter.

Figure 2:
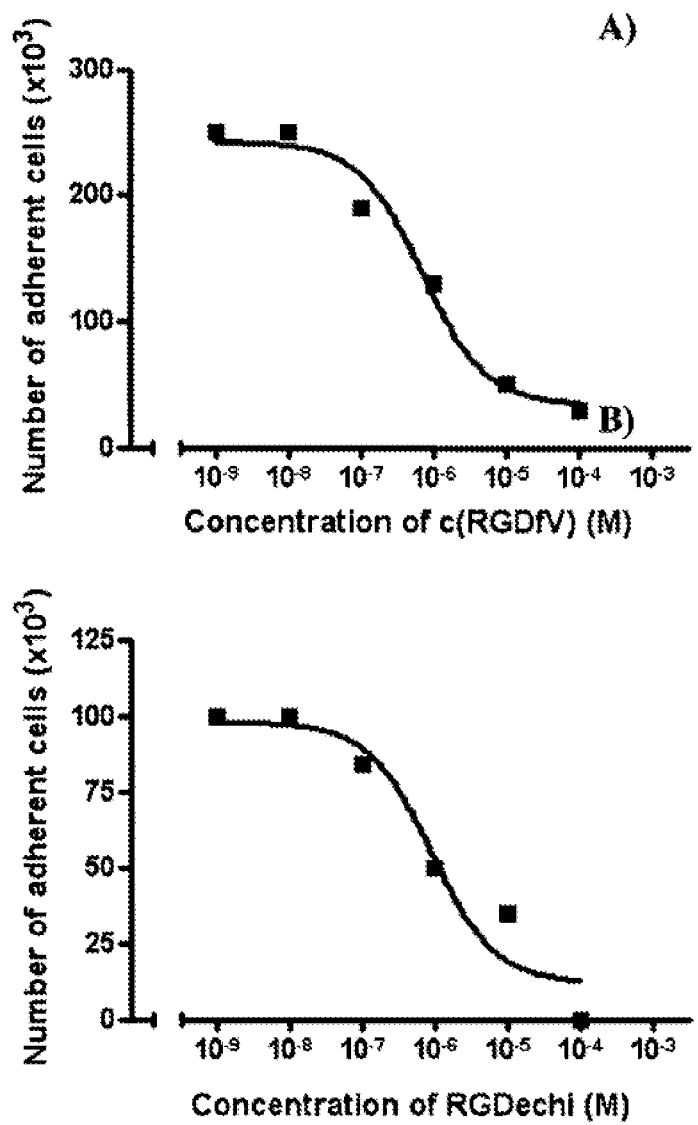
FIG. 2. Shows representative inhibition curves obtained from adhesion assays performed in K$\alpha_v\beta_3$ cells. Cells were preincubated with increasing concentrations of c(RGDfV) (panel A, $IC_{50}$ 0.68 µM) and RGDechi (panel B, $IC_{50}$ 0.88 µM) for 1 h at 4° C. and then seeded on vitronectin-coated plates. Cells were allowed to adhere for 1 h at 37° C. and finally counted.

All synthesized peptides were tested for their ability to inhibit cell adhesion to vitronectin. Human erythroleukemia K562 cells overexpressing $α_vβ_3$ ($Kα_vβ_3$) were incubated with increasing concentrations of the tested peptide and then allowed to adhere to vitronectin-coated plates. Both c(RGDfV) (Sulyok, G. A.; et al. *J. Med. Chem.* 2001, 44, 1938-1950; Dechantsreiter, M. A.; et al *J. Med. Chem.* 1999, 42, 3033-3040), a c(RGDf[NMe]V) analogue with comparable biological activity, and RGDechi were able to inhibit adhesion of $Kα_vβ_3$ cells to vitronectin. FIG. 2 shows representative inhibition curves obtained by incubating $Kα_vβ_3$ with c(RGDfV) and RGDechi, respectively. The $IC_{50}$ value for c(RGDfV) ranged between 0.64 µM and 3.48 µM, whereas the $IC_{50}$ of RGDechi ranged between 0.79 µM and 7.59 µM. RGDechi fragments were tested for their ability to inhibit $Kα_vβ_3$ cell adhesion. Incubation with 10 µM of selected amino acid sequences, such as echi 11-19 (SEQ ID NO: 3), echi6-19 (SEQ ID NO: 2) and echiL (SEQ ID NO: 1), failed to inhibit cell adhesion, which remained 97.5%, 99.0%, and 89.5% as compared to untreated control cells.

Figure 3:
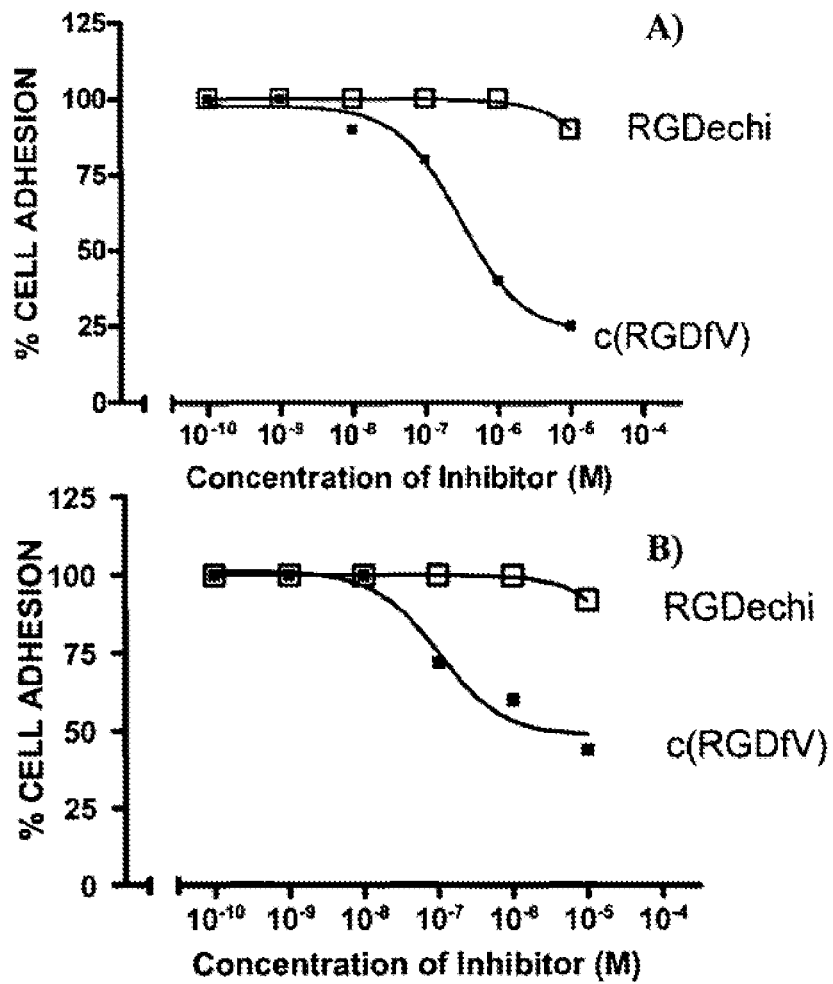
FIG. 3. Shows selectivity of RGDechi for $\alpha_v\beta_3$. Panel A. Representative inhibition curves obtained from adhesion assays performed in K$\alpha_v\beta_5$ cells. Cells were preincubated with increasing concentrations of c(RGDfV) (closed squares) and RGDechi (open squares) for 1 h at 4° C. and adhesion was determined as described in FIG. 2. The results are expressed as the percentage of adherent cells considering the untreated control sample as 100%. Panel B Representative inhibition curves obtained from adhesion assays performed in K$\alpha_{IIb}\beta_3$ cells. Cells were pre-incubated with anti-$\alpha_v\beta_3$ blocking LM609 monoclonal antibody and subjected to the adhesion assay on fibrinogen (10 µg/mL).

To test the selectivity of binding of the novel peptide RGDechi, □ $α_vβ_5$ overexpressing cells ($Kα_vβ_5$) were used in the adhesion assay. In FIG. 3A representative inhibition curves are reported. While c(RGDfV) was able to efficiently inhibit adhesion of cells to vitronectin, RGDechi did not show any significant inhibitory effect on $Kα_vβ_5$ cell adhesion, indicating lack of cross-reactivity with $α_vβ_5$. In parallel experiments, $\alpha_{IIb}\beta_3$ overexpressing cells were pre-incubated with LM609 monoclonal antibody and then allowed to adhere to fibrinogen in the presence or absence of the selected peptide. FIG. 3B shows that, while c(RGDfV) was able to efficiently inhibit adhesion of cells to fibrinogen, RGDechi did not show any significant inhibitory effect on $\alpha_{IIb}\beta_3$ overexpressing cells.

Consistent results were obtained from competition binding experiments indicating that the novel peptide RGDechi efficiently competes with a c(RGDf[NMe]V) analogue labeled with $^{125}$I [c(RGDyV)] for the binding to $\alpha_v\beta_3$ overexpressing cells and not to $\alpha_v\beta_5$ overexpressing clones.

In conclusion, the above results show that the RGDechi chimeric peptide is a novel and selective ligand for $\alpha_v\beta_3$ integrin.

AA1 is an alpha amino acid selected in the group of Cys, Asp, Glu, Lys, Orn, Pen, Dab or Dap;

AA2 is an alpha amino acid selected in the group of Cys, Asp, Glu, Lys, Orn, Pen, Dab or Dap;

L is a linker sequence consisting of a number of amino acid residues comprised between 0 and 2, such as the sequence PG;

(Xaa)n is an amino acid sequence in which n ranges from 1 to 3, which sequence is substantially homologue to that of sequence 28-30 of Echistatin: MDD (Yaa)m is an amino acid sequence in which m ranges from 2 to 9, which sequence is substantially homologue to that of C-terminus (41-49) of Echistatin: RNPHKGPAT (SEQ ID NO:3).

The invention claimed is:

1. An antagonist compound of $\alpha_v\beta_3$ integrin, displaying a selective affinit for $\alpha_v\beta_3$ integrin, containing a cyclic RGD motif and two echistatin C-terminal moieties covalently linked by a spacer sequence having the following formula (I):

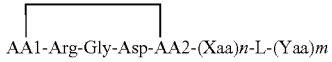

(I)

wherein:

2. A pharmaceutical composition comprising a therapeutically effective amount of the $\alpha_v\beta_3$ antagonist compound of claim 1 and a pharmaceutically acceptable excipient.

3. A pharmaceutical composition comprising a therapeutically effective amount of the compound of claim 1 and a pharmaceutically acceptable excipient.

4. The antagonist compound according to claim 1, wherein the cyclic RGD motif is a cyclic peptide in which the ring consists solely of amino-acid residues in peptide linkages.

5. The antagonist compound according to claim 1, wherein the cyclic RGD motif is obtainable by formation of a peptide bond between terminal residues of a linear peptide.

6. An antagonist compound of $\alpha_v\beta_3$ integrin, displaying a selective affinity for $\alpha_v\beta_3$ integrin, containing a pentapeptide cyclic RGD motif and two echistatin C-terminal moieties covalently linked by a spacer sequence.

7. A method of treating a disorder comprising administering a therapeutically effective amount of the alpha v beta 3 antagonist compound of claim 1 to a patient in need thereof.

8. The method of claim 7 wherein the disorder is a pathology related to angiogenesis and metastasis, such as breast cancer, musculoskeletal tumors, melanoma, head and neck cancer, human glioma, cervical cancer, vascular restenosis, osteoporosis, rheumatoid arthritis.

9. The method of claim 7 wherein treatment is aimed at decreasing the proliferation of tumor cells.

10. The method of claim 7 wherein treatment is aimed at modulating pathologic angiogenesis.

11. A method of treating a disorder comprising administering a therapeutically effective amount of the compound of claim 1 to a patient in need thereof.

* * * * *

SEQUENCE LISTING

```
<160> NUMBER OF SEQ ID NOS: 3

<210> SEQ ID NO 1
<211> LENGTH: 19
<212> TYPE: PRT
<213> ORGANISM: Artificial sequence
<220> FEATURE:
<223> OTHER INFORMATION: Synthetic polypeptide

<400> SEQUENCE: 1

Lys Arg Gly Asp Glu Met Asp Asp Pro Gly Arg Asn Pro His Lys Gly
1               5                   10                  15

Pro Ala Thr

<210> SEQ ID NO 2
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 2

Met Asp Asp Pro Gly Arg Asn Pro His Lys Gly Pro Ala Thr
1               5                   10

<210> SEQ ID NO 3
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 3

Arg Asn Pro His Lys Gly Pro Ala Thr
1               5
```